US009763685B2

(12) United States Patent
Batchelor et al.

(10) Patent No.: US 9,763,685 B2
(45) Date of Patent: Sep. 19, 2017

(54) COMBINATION MEDICAL DEVICE

(71) Applicant: Gyrus ACMI, Inc., Southborough, MA (US)

(72) Inventors: Kester J. Batchelor, Mound, MN (US); Richard J. Curtis, Maple Grove, MN (US); Ryan J. Windgassen, Nowthen, MN (US)

(73) Assignee: Gyrus ACMI, Inc., Southborough, MA (US)

( * ) Notice: Subject to any disclaimer, the term of this patent is extended or adjusted under 35 U.S.C. 154(b) by 364 days.

(21) Appl. No.: 14/593,546

(22) Filed: Jan. 9, 2015

(65) Prior Publication Data

US 2016/0199082 A1 Jul. 14, 2016

(51) Int. Cl.
| | |
|---|---|
| *A61B 17/28* | (2006.01) |
| *A61B 18/14* | (2006.01) |
| *A61B 17/30* | (2006.01) |
| A61B 18/00 | (2006.01) |
| A61B 17/3211 | (2006.01) |

(52) U.S. Cl.
CPC ...... *A61B 17/2816* (2013.01); *A61B 17/2804* (2013.01); *A61B 17/30* (2013.01); *A61B 18/1445* (2013.01); *A61B 17/3211* (2013.01); *A61B 2018/00589* (2013.01); *A61B 2018/00595* (2013.01); *A61B 2018/1412* (2013.01)

(58) Field of Classification Search
CPC . A61B 17/2804; A61B 17/2816; A61B 28/30; A61B 28/3211; A61B 18/1445; A61B 2018/00589; A61B 2018/00595

USPC .................................................... 606/50–52
See application file for complete search history.

(56) References Cited

U.S. PATENT DOCUMENTS

| | | | |
|---|---|---|---|
| 3,576,072 A | 4/1971 | Foster | |
| 3,906,957 A | 9/1975 | Weston | |
| 4,023,450 A | 5/1977 | Ygfors | |
| 4,387,610 A | 6/1983 | Sergeant | |
| 4,839,947 A | 6/1989 | Cohen et al. | |
| 5,236,436 A * | 8/1993 | Koros | A61B 17/062 606/148 |
| 5,312,420 A | 5/1994 | Toso et al. | |
| 6,361,534 B1* | 3/2002 | Chen | A61B 17/2804 606/170 |
| 8,491,624 B2* | 7/2013 | Kerr | A61B 17/29 606/205 |
| 9,333,049 B2* | 5/2016 | McDonald | A61C 3/10 |
| 2002/0072752 A1* | 6/2002 | Zucherman | A61B 17/7074 606/99 |
| 2002/0106609 A1 | 8/2002 | Palermo et al. | |

(Continued)

FOREIGN PATENT DOCUMENTS

EP 2022415 A1 2/2009

*Primary Examiner* — Michael Peffley
(74) *Attorney, Agent, or Firm* — Vivacqua Law, PLLC; Gerald P. Kazanjian

(57) ABSTRACT

A combination medical includes a first arm and a second arm interconnected to the first arm. The first arm and the second arm are biased towards each other by a closing force. A biasing member is disposed between the first arm and the second arm. The biasing member has a first position that biases the first arm and the second arm away from each other against the closing force and a second position that does not oppose the closing force. The combination medical device may be an electrosurgical device with a mono-polar and bi-polar configuration.

4 Claims, 14 Drawing Sheets

(56) References Cited

U.S. PATENT DOCUMENTS

| | | |
|---|---|---|
| 2003/0083747 A1 | 5/2003 | Winterbottom et al. |
| 2003/0225416 A1* | 12/2003 | Bonvallet ............ A61B 17/025 606/105 |
| 2006/0190035 A1 | 8/2006 | Hushka et al. |
| 2010/0280533 A1 | 11/2010 | Martinez et al. |
| 2012/0303025 A1 | 11/2012 | Garrison |
| 2013/0004914 A1 | 1/2013 | Marteney et al. |
| 2013/0178852 A1 | 7/2013 | Allen, IV et al. |
| 2014/0276795 A1 | 9/2014 | Batchelor et al. |

* cited by examiner

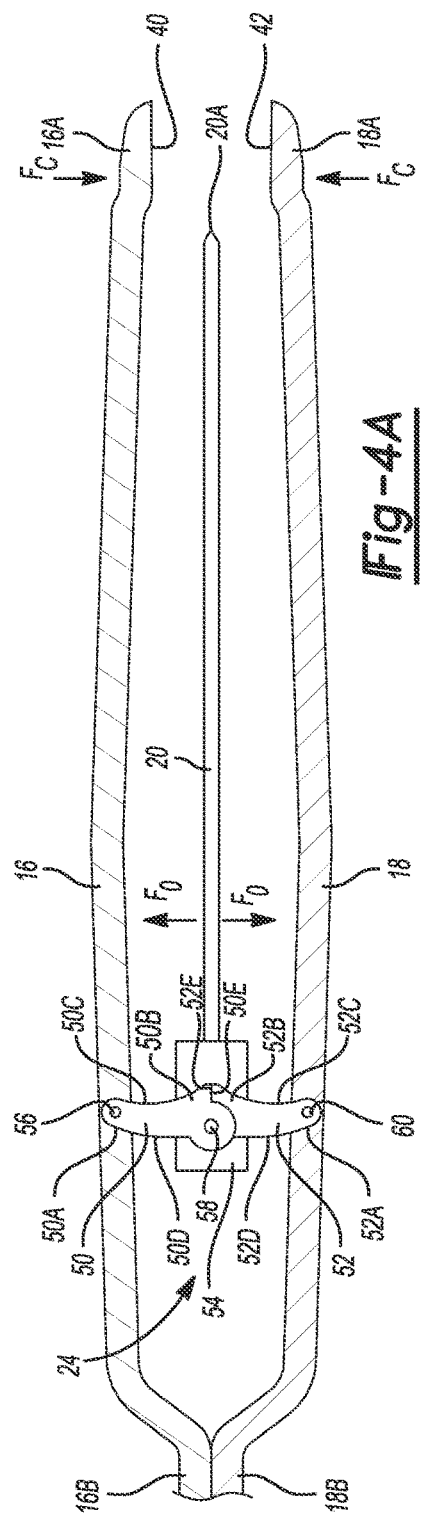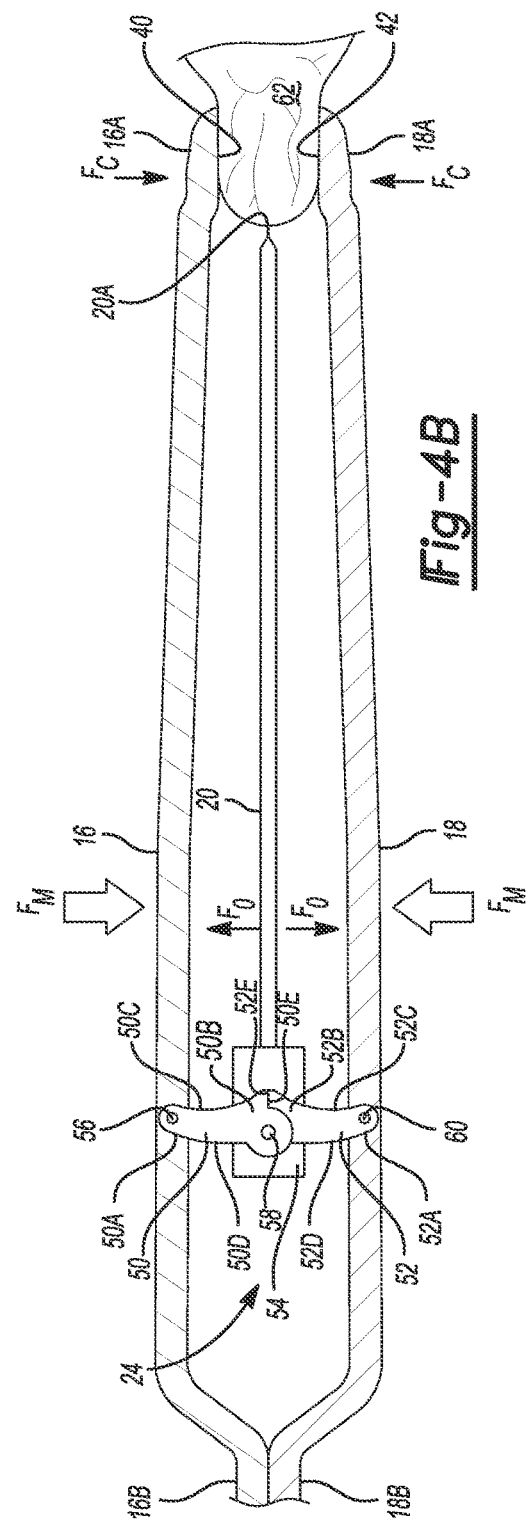

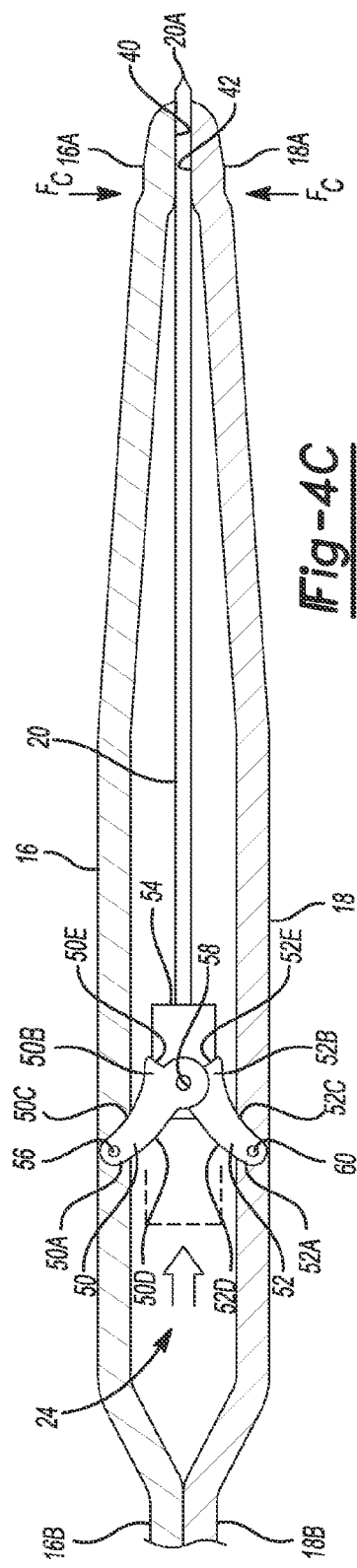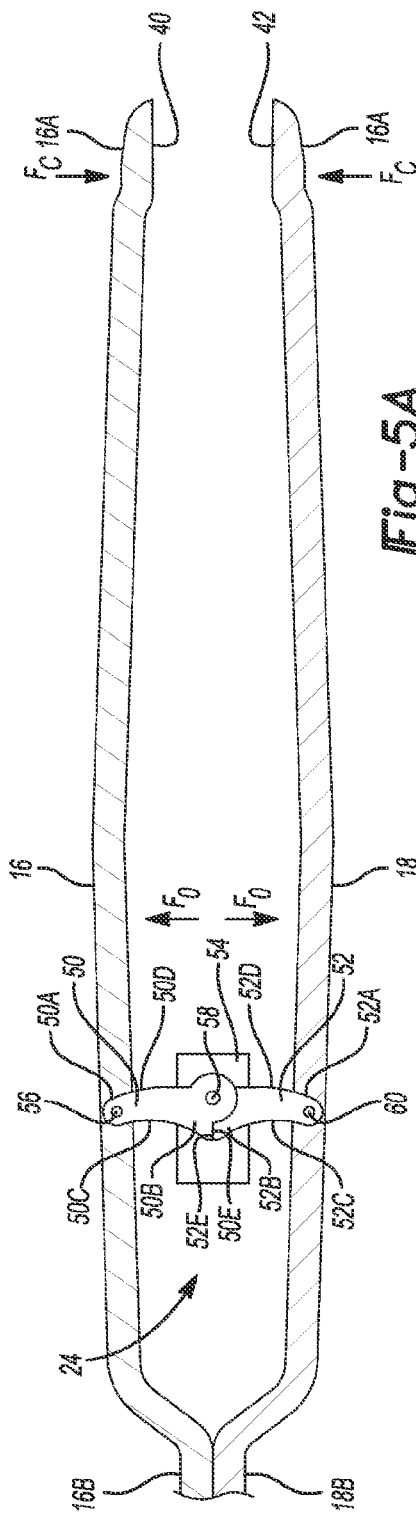

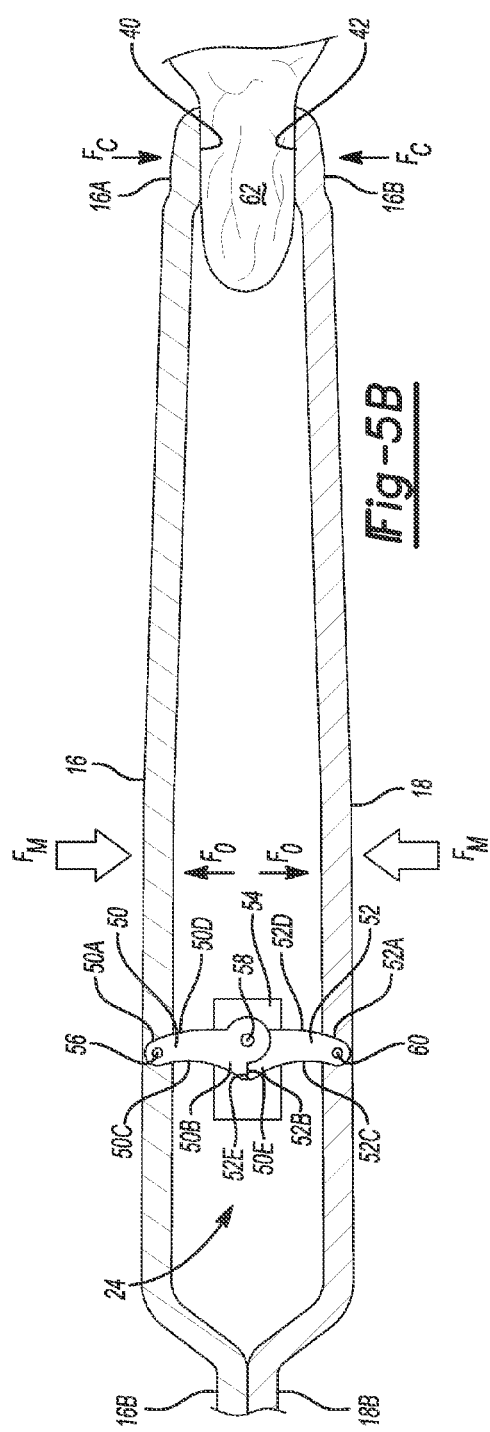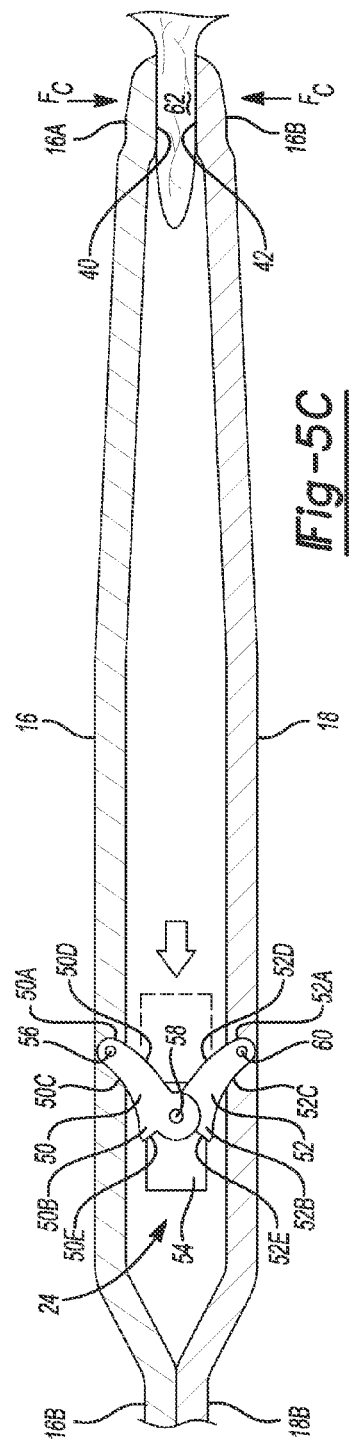

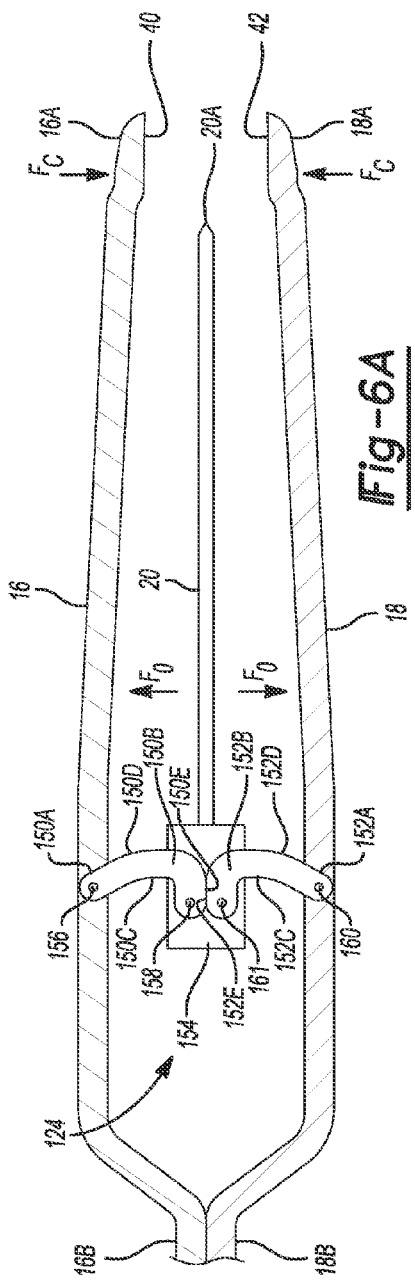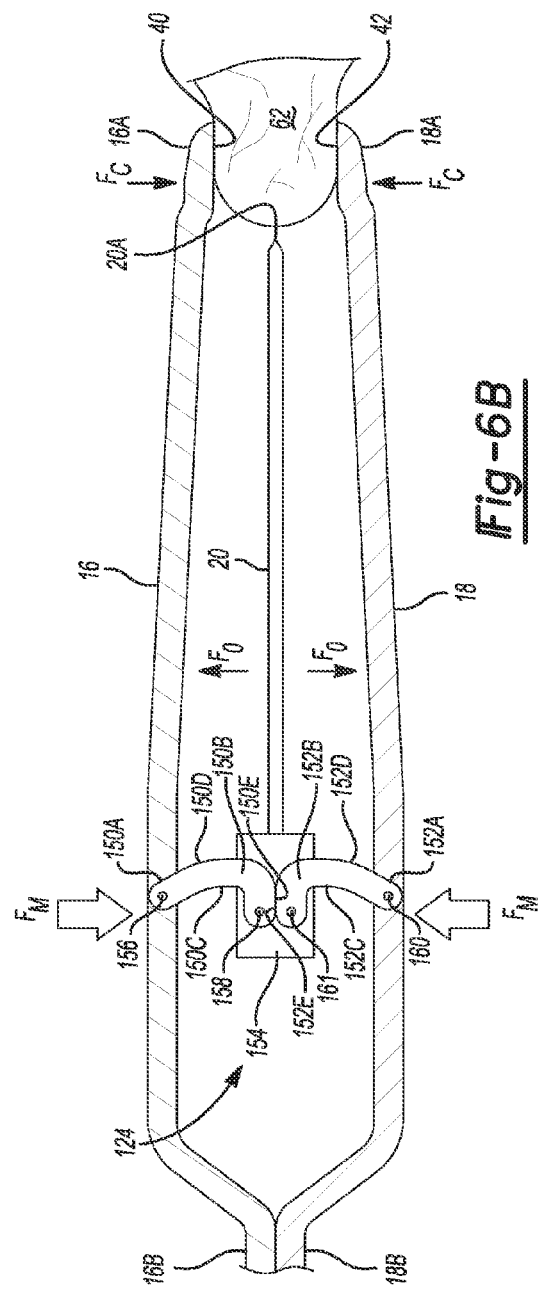

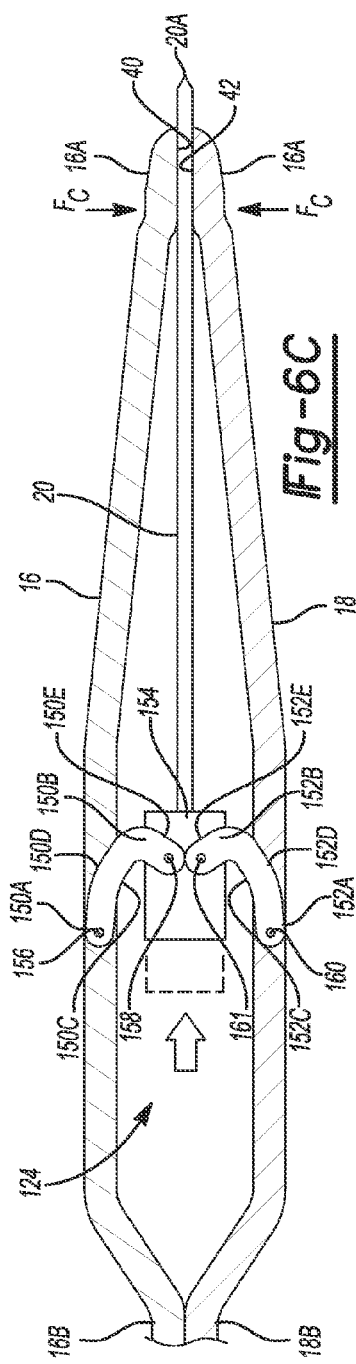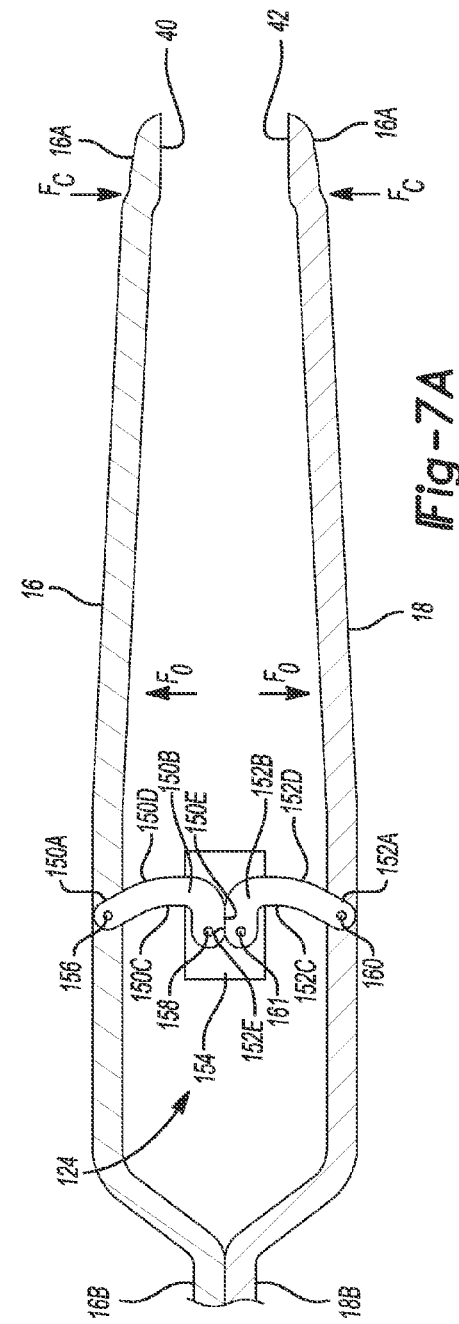

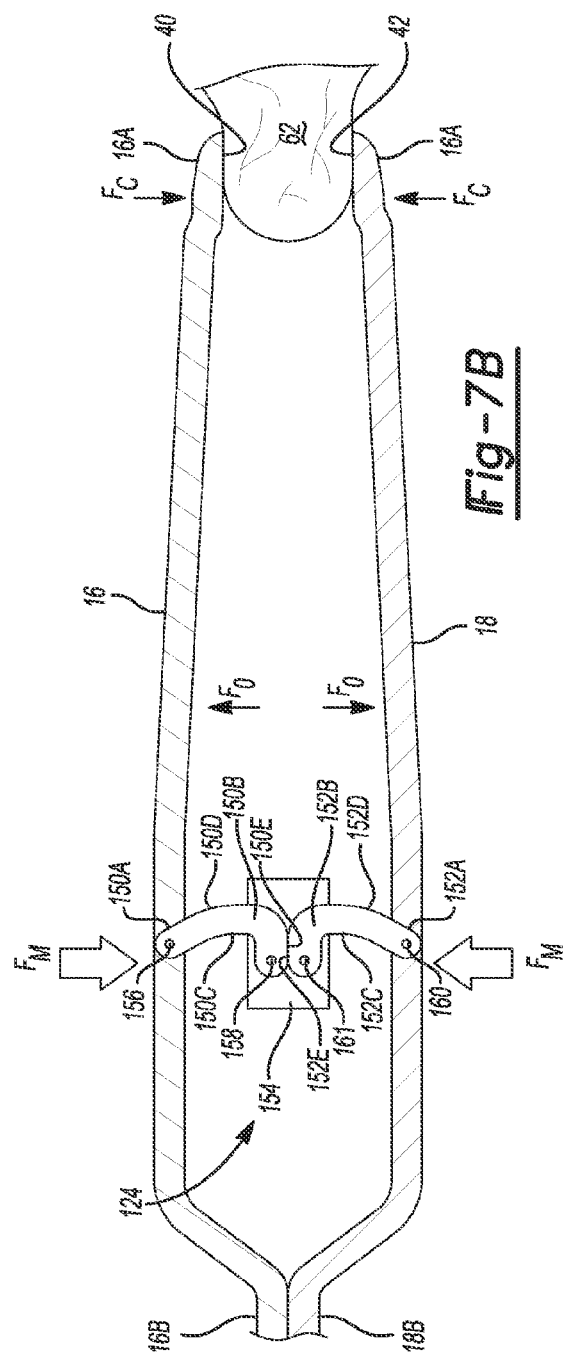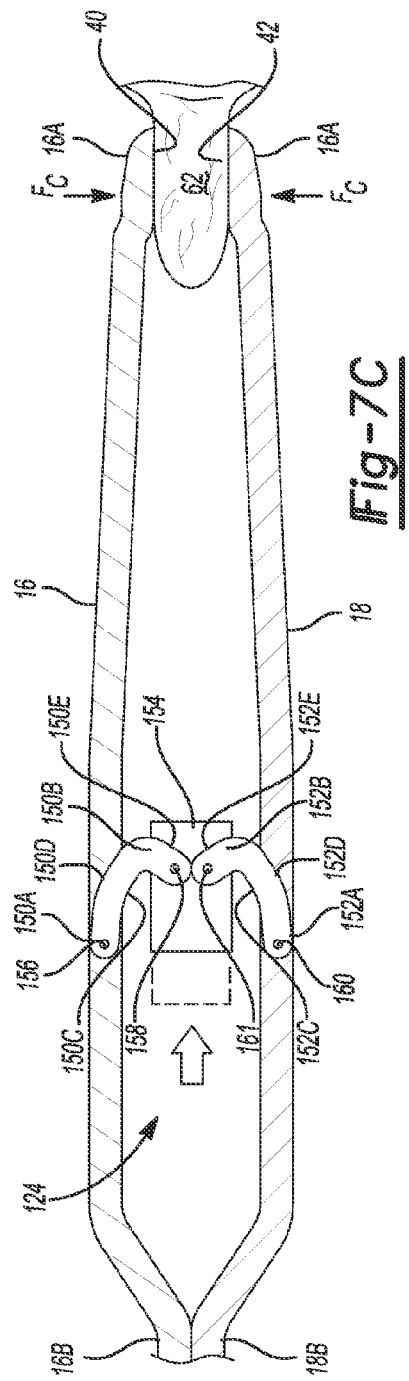

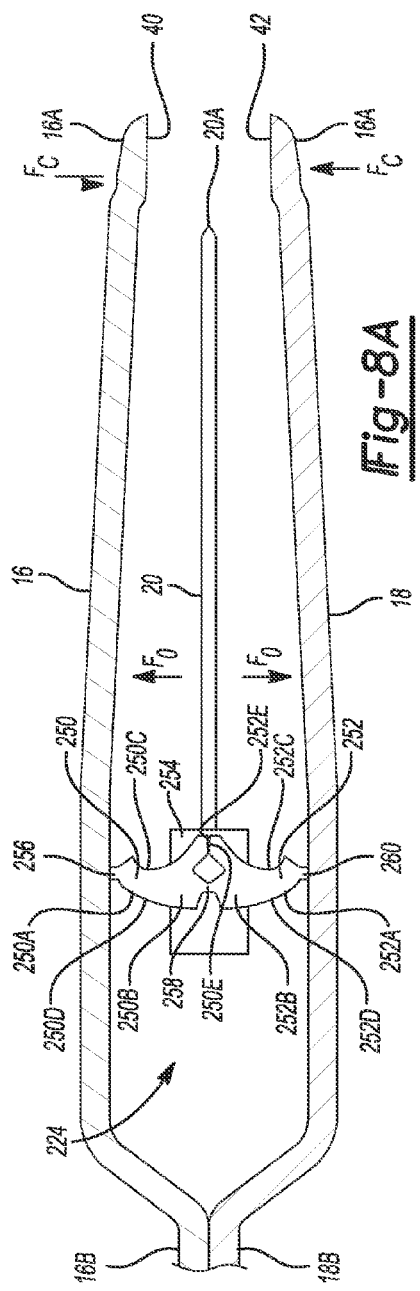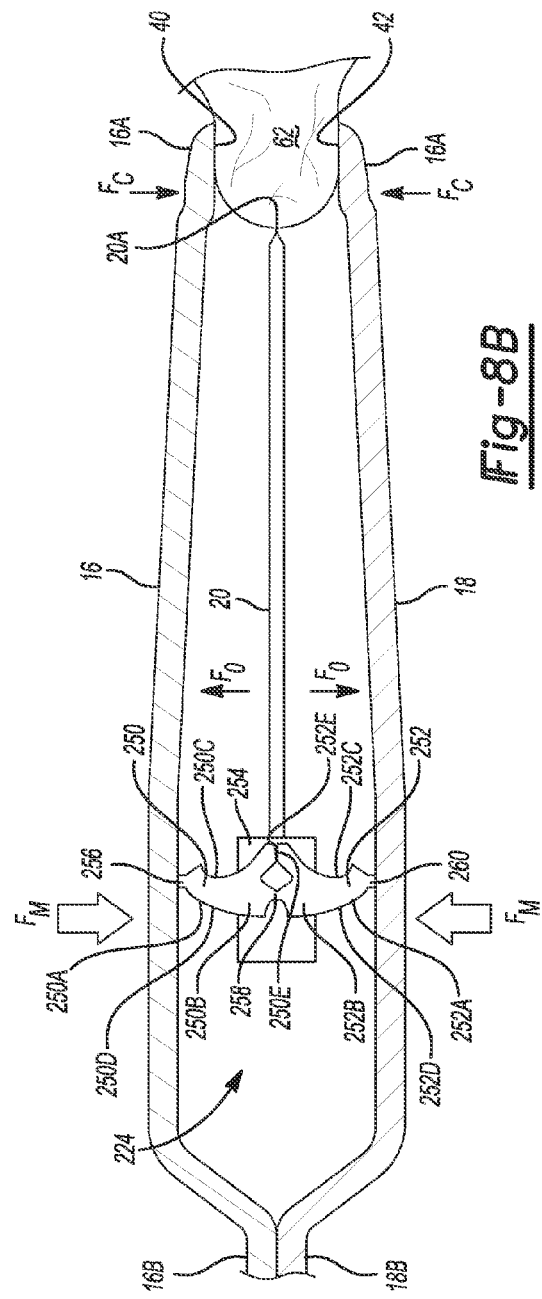

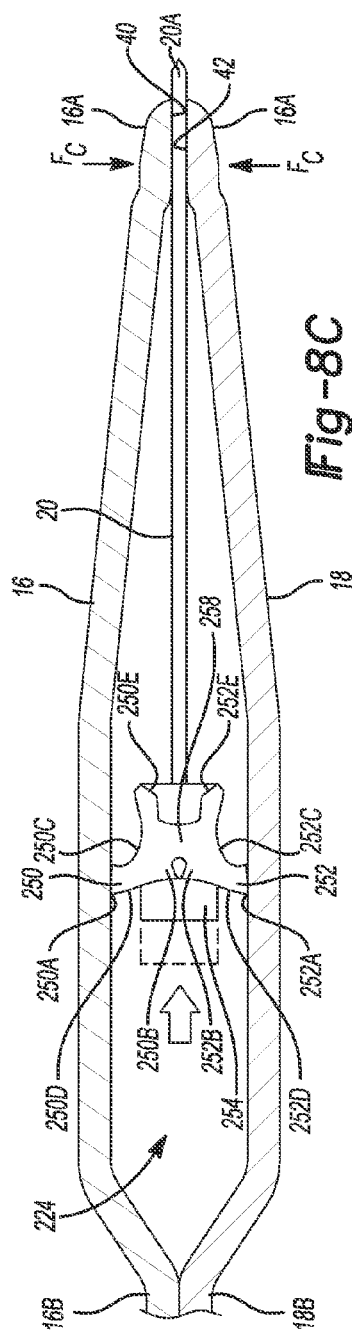
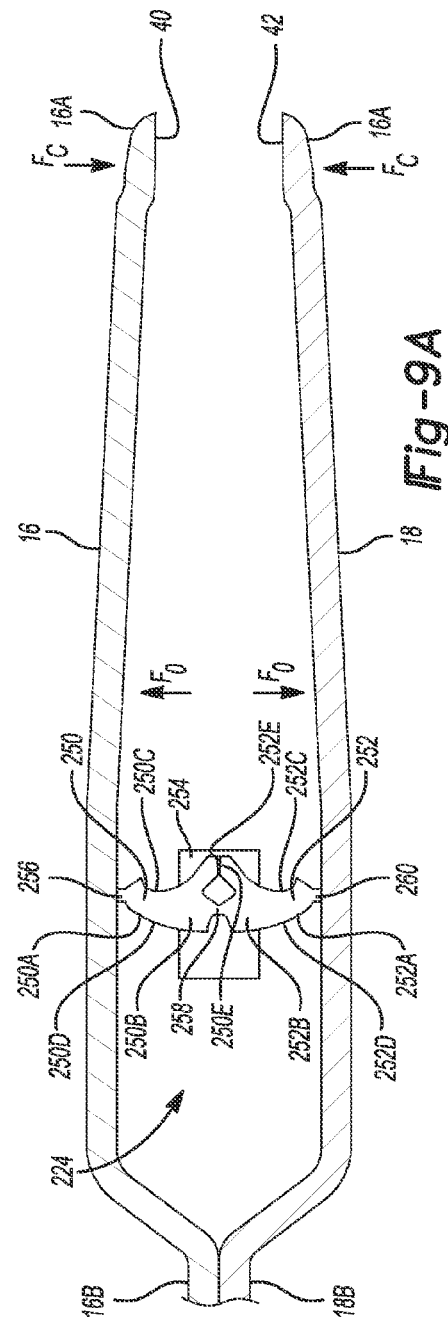

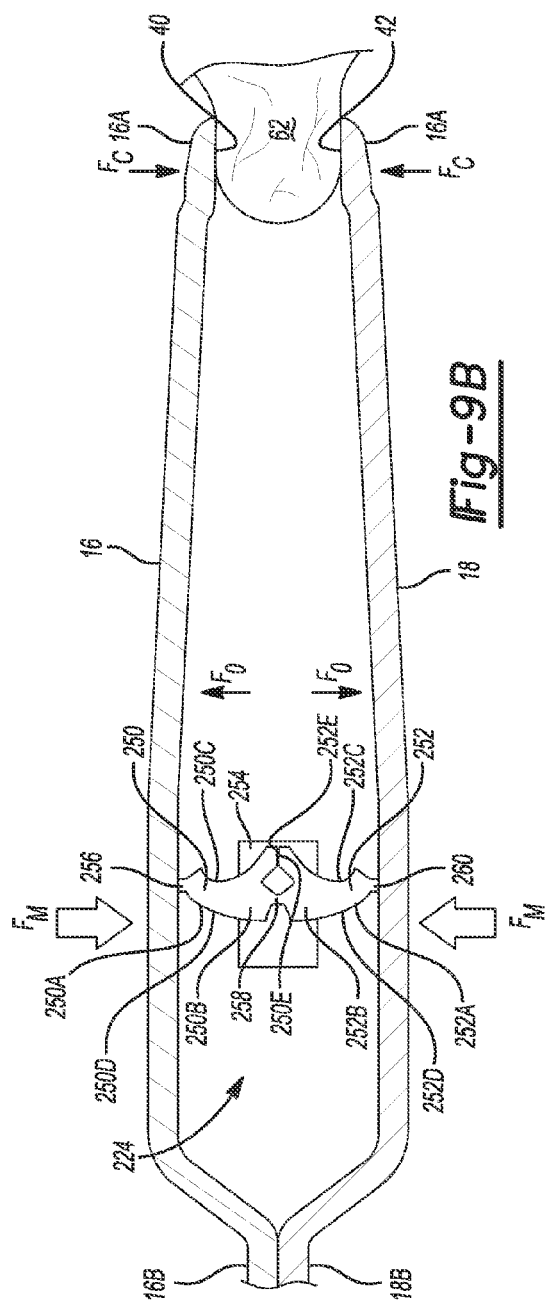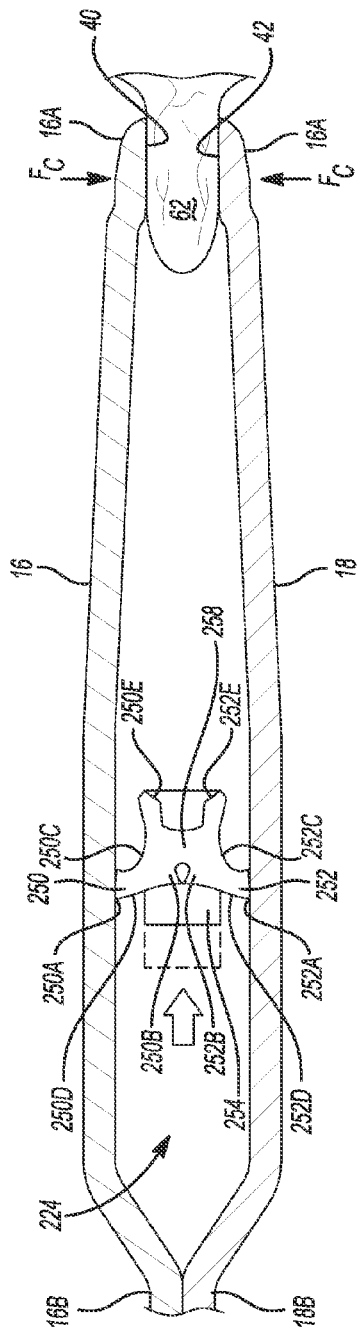

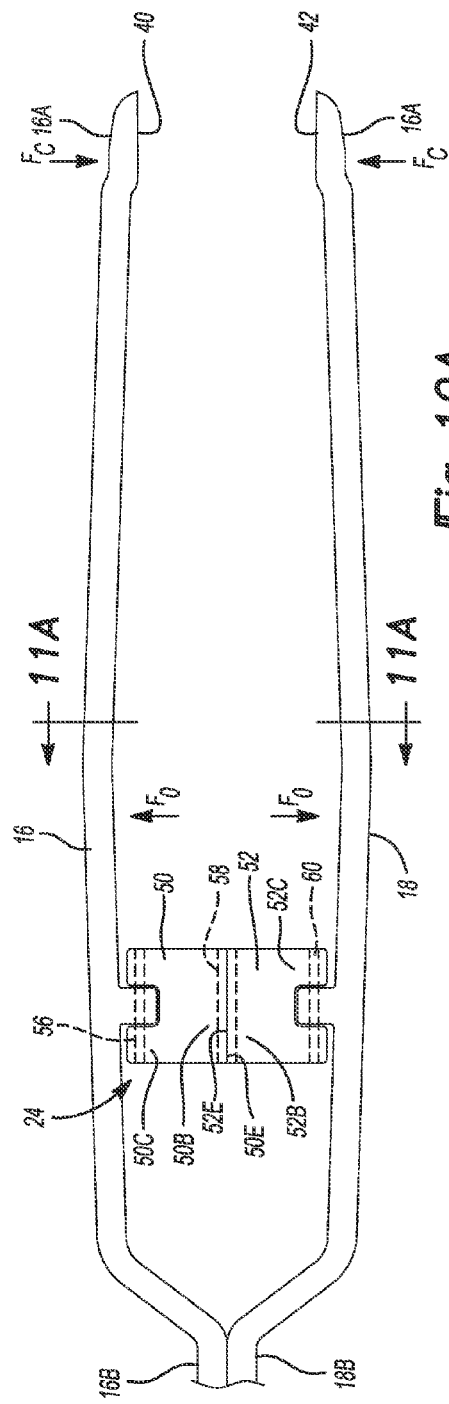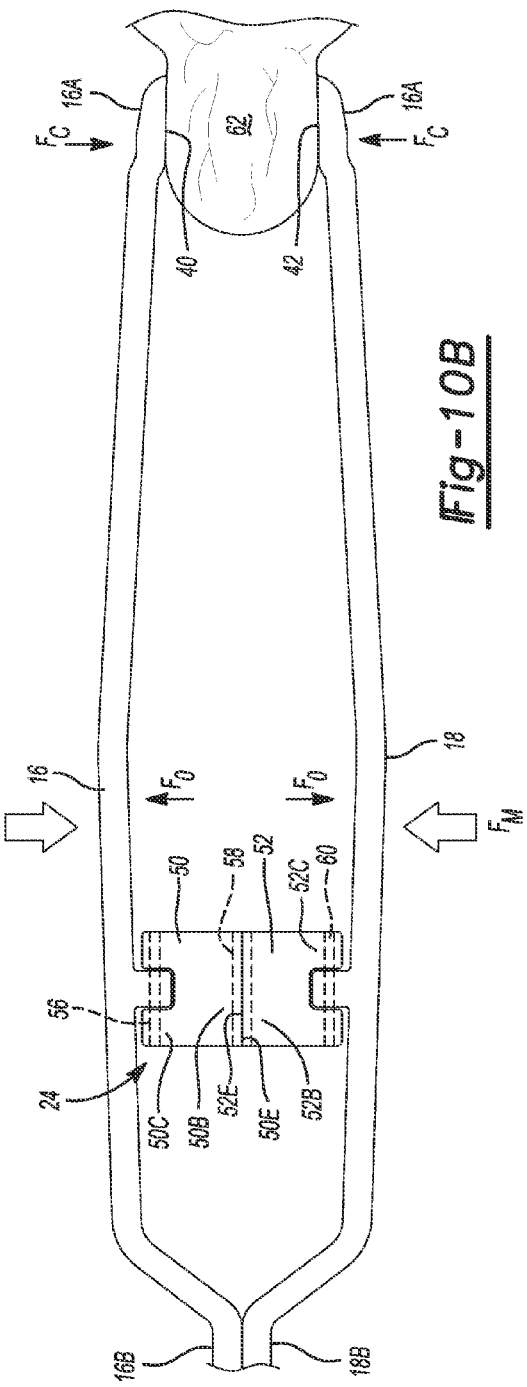

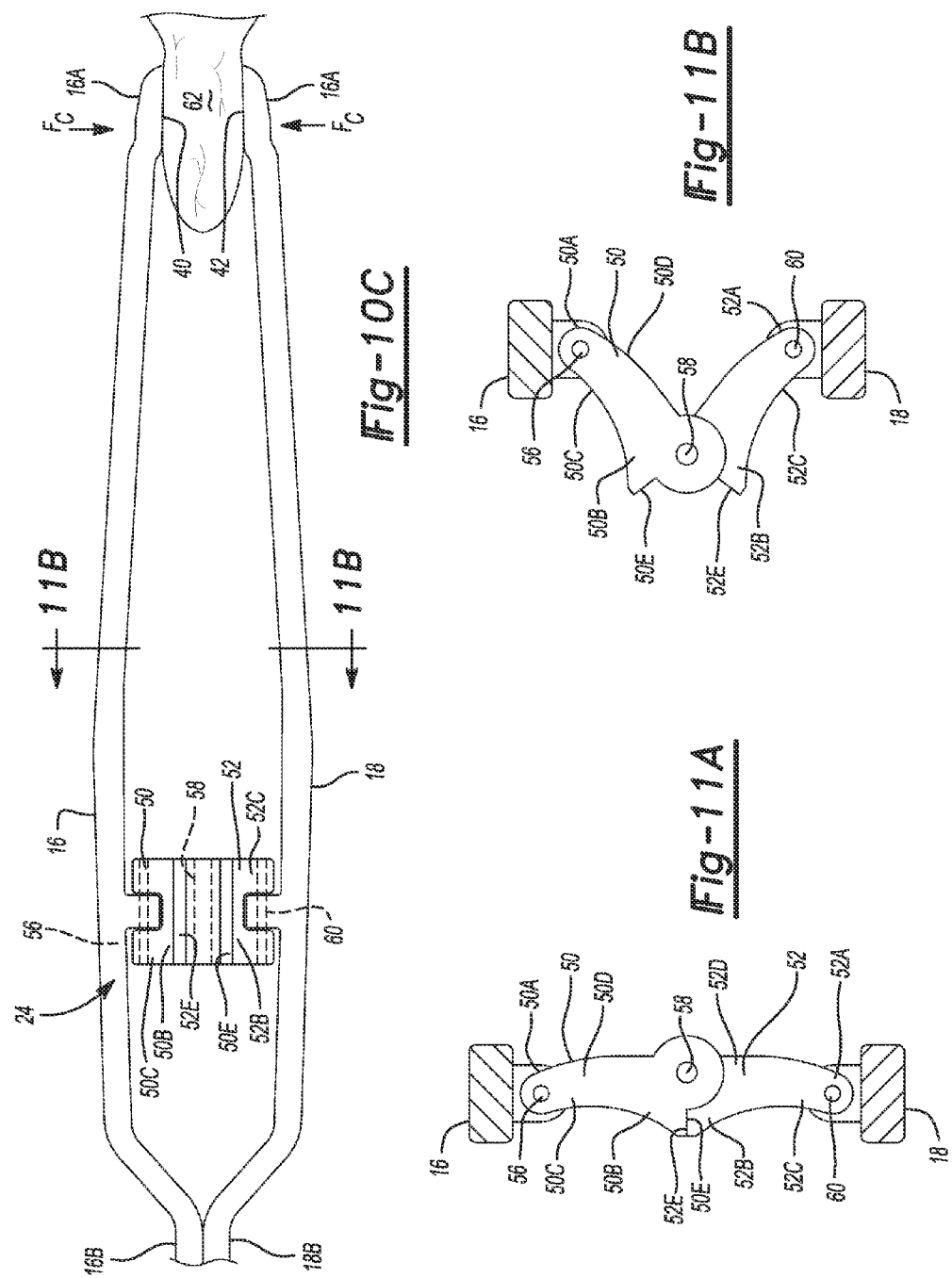

COMBINATION MEDICAL DEVICE

FIELD

The present disclosure generally relates to a combination medical device having multiple modes of operation, and more specifically to a combination electrosurgical forceps or tweezers having a first configuration with a constant closure force and a second configuration having a variable, manual closure force.

BACKGROUND

The statements in this section merely provide background information related to the present disclosure and may or may not constitute prior art.

A typical electrosurgery device utilizes a therapy current to treat a patient, either in a mono-polar configuration or a bi-polar configuration. The therapy current is used to cut, perform hemostasis on, coagulate, desiccate, fulgurate, or electro cauterize the tissue of a patient during surgery. The device itself may have various configurations and may be combined with a tweezers or forceps arrangement to grip or grasp the tissue. For example, such an electrosurgical device generally includes a pair of substantially rigid arms that each terminate in grips or jaws. Opposite the jaws, the pair of arms are attached together, either directly or through a hinge, to form a fulcrum on which the pair of arms pivot. Typically, the arms are biased away from each other into an open position. Compression of the arms forces the jaws to come together to grip the tissue. The device may lock onto or latch onto the tissue without the user having to apply finger pressure. The therapy current, supplied from a power source such as a generator or wall plug, is directed through one (mono-polar configuration) or both (bi-polar configuration) of the arms. An example of a combination electrosurgical device is disclosed in commonly assigned U.S. Publication No. 2014/0276795 filed on Mar. 12, 2014, herein incorporated by reference in its entirety.

The known cross section of users of electrosurgery devices range from expert users, who use these devices daily and specialize in a few procedures, to general users who use these devices sporadically and are not considered expert in their use. Thus, for a general user, it is desirable to reduce the skill requirements of a particular procedure in order to allow the general user to concentrate on more complex surgery and on the pathology as it is presented. Furthermore, it is generally desirable for all users to have consistent device performance to help reduce the readmissions into surgery. Therefore, there is a need in the art to provide a combination electrosurgical medical device that assists surgeons by providing a consistent compressive force (a force that can be validated by the manufacture) to seal vessels consistently of specific sizes, while also providing various modes of operation.

SUMMARY

A combination medical device according to the principles of the present invention is provided. The device includes a first arm and a second arm interconnected to the first arm. The arms may terminate in teeth or any other surface suitable for gripping. The first arm and the second arm are biased towards each other by a closing force. A biasing member is disposed between the first arm and the second arm. The biasing member has a first position that biases the first arm and the second arm away from each other against the closing force and a second position that does not oppose the closing force.

In one aspect, the biasing member includes a first connector pivotally connected to the first arm and a second connector pivotally connected to the second arm, and the first connector is pivotally connected to the second connector.

In another aspect, the first connector has a first surface, the second connector has a second surface, and the first surface contacts the second surface when the biasing member is in the first position.

In another aspect, the first arm has a first distal end and a first proximate end, the second arm has a second distal end and a second proximate end, and the first proximate end is interconnected to the second proximate end to bias the first distal end and the second distal end towards one another.

In another aspect, the first connector is connected to the second connector at a pivot point.

In another aspect, the pivot point remains on a plane defined by the first arm and the second arm when the biasing member is in the first position and the second position.

In another aspect, the pivot point is closer to the first and second proximate ends when in the first position than when in the second position.

In another aspect, the pivot point is closer to the first and second distal ends when in the first position than when in the second position.

In another aspect, a blade is connected at the pivot point, wherein the blade is extended past the first and second distal ends when the biasing member is in the second position and wherein the blade does is not extended past the first and second distal ends when the biasing member is in the first position.

In another aspect, the device is connectable to a power source and the device includes a first operating condition that communicates a first electrical current through either the first arm, the second arm, or both, and a second operating condition that communicates a second electrical current through the blade.

In another aspect, the pivot point is not on a plane defined by the first arm and the second arm when the biasing member is in at least one of the first position and the second position.

In another aspect, at least one of the first arm, the second arm, the first connector, and the second connector are resilient.

In another aspect, the first arm and the second arm are resilient and the first connector and the second connector are rigid.

In another aspect, the first arm and the second arm are rigid and the first connector and the second connector are resilient.

In another aspect, the first arm, the second arm, the first connector and the second connector are all resilient.

Further features, aspects, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4A is a cross-section, schematic view of the combination medical device in the first mode of operation;

FIG. 4B is a cross-section, schematic view of the combination medical device in the first mode of operation under a manual load;

FIG. 4C is a cross-section, schematic view of the combination medical device in the second mode of operation;

FIG. 5A is a cross-section, schematic view of another embodiment of the combination medical device in a first mode of operation;

FIG. 5B is a cross-section, schematic view of the combination medical device in the first mode of operation under a manual load;

FIG. 5C is a cross-section, schematic view of the combination medical device in a second mode of operation;

FIG. 6A is a cross-section, schematic view of another embodiment of the combination medical device in a first mode of operation;

FIG. 6B is a cross-section, schematic view of the combination medical device in the first mode of operation under a manual load;

FIG. 6C is a cross-section, schematic view of the combination medical device in a second mode of operation;

FIG. 7A is a cross-section, schematic view of another embodiment of the combination medical device in a first mode of operation;

FIG. 7B is a cross-section, schematic view of the combination medical device in the first mode of operation under a manual load;

FIG. 7C is a cross-section, schematic view of the combination medical device in a second mode of operation;

FIG. 8A is a cross-section, schematic view of another embodiment of the combination medical device in a first mode of operation;

FIG. 8B is a cross-section, schematic view of the combination medical device in the first mode of operation under a manual load;

FIG. 8C is a cross-section, schematic view of the combination medical device in a second mode of operation;

FIG. 9A is a cross-section, schematic view of another embodiment of the combination medical device in a first mode of operation;

FIG. 9B is a cross-section, schematic view of the combination medical device in the first mode of operation under a manual load;

FIG. 9C is a cross-section, schematic view of the combination medical device in a second mode of operation;

FIG. 10A is a cross-section, schematic view of another embodiment of the combination medical device in a first mode of operation;

FIG. 10B is a cross-section, schematic view of the combination medical device in the first mode of operation under a manual load;

FIG. 10C is a cross-section, schematic view of the combination medical device in a second mode of operation;

FIG. 11A is a cross-section view of the combination medical device viewed in the direction of arrows 11A-11A shown in FIG. 10A; and FIG. 11B is a cross-section view of the combination medical device viewed in the direction of arrows 11B-11B shown in FIG. 10C.

DETAILED DESCRIPTION

The following description is merely exemplary in nature and is not intended to limit the present disclosure, application, or uses.

Figure 1:
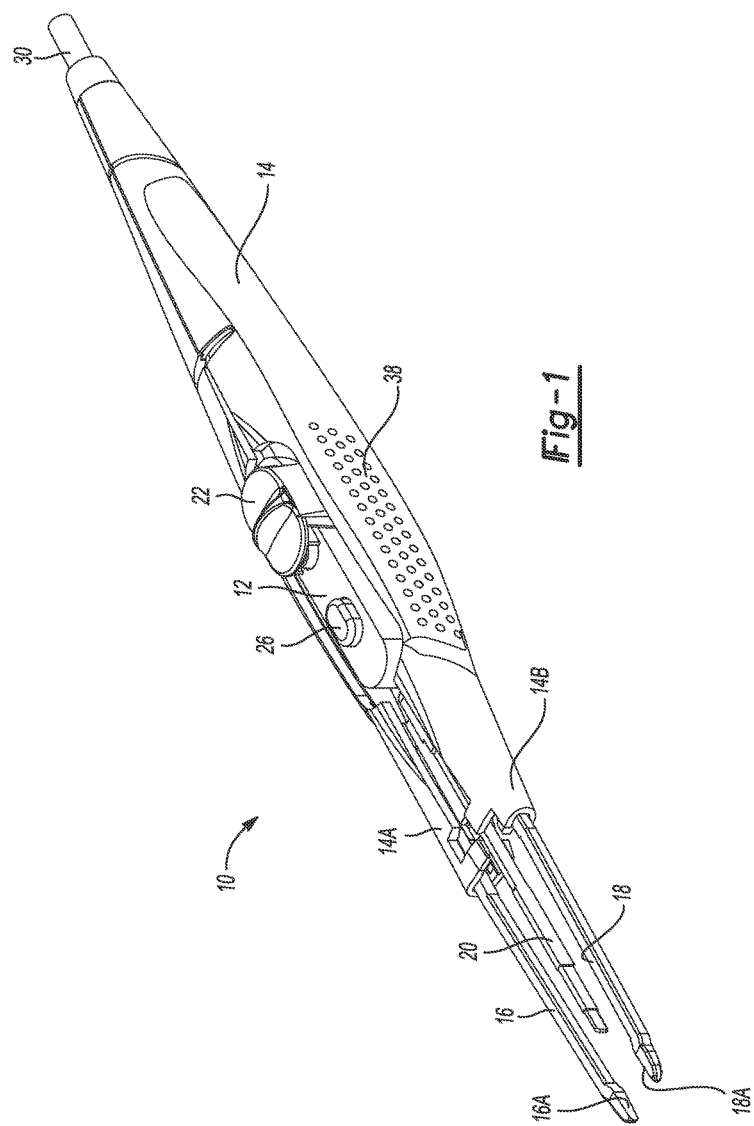
FIG. 1 is a front perspective view of a combination medical device in a first mode of operation according to the principles of the present invention.
Figure 2:
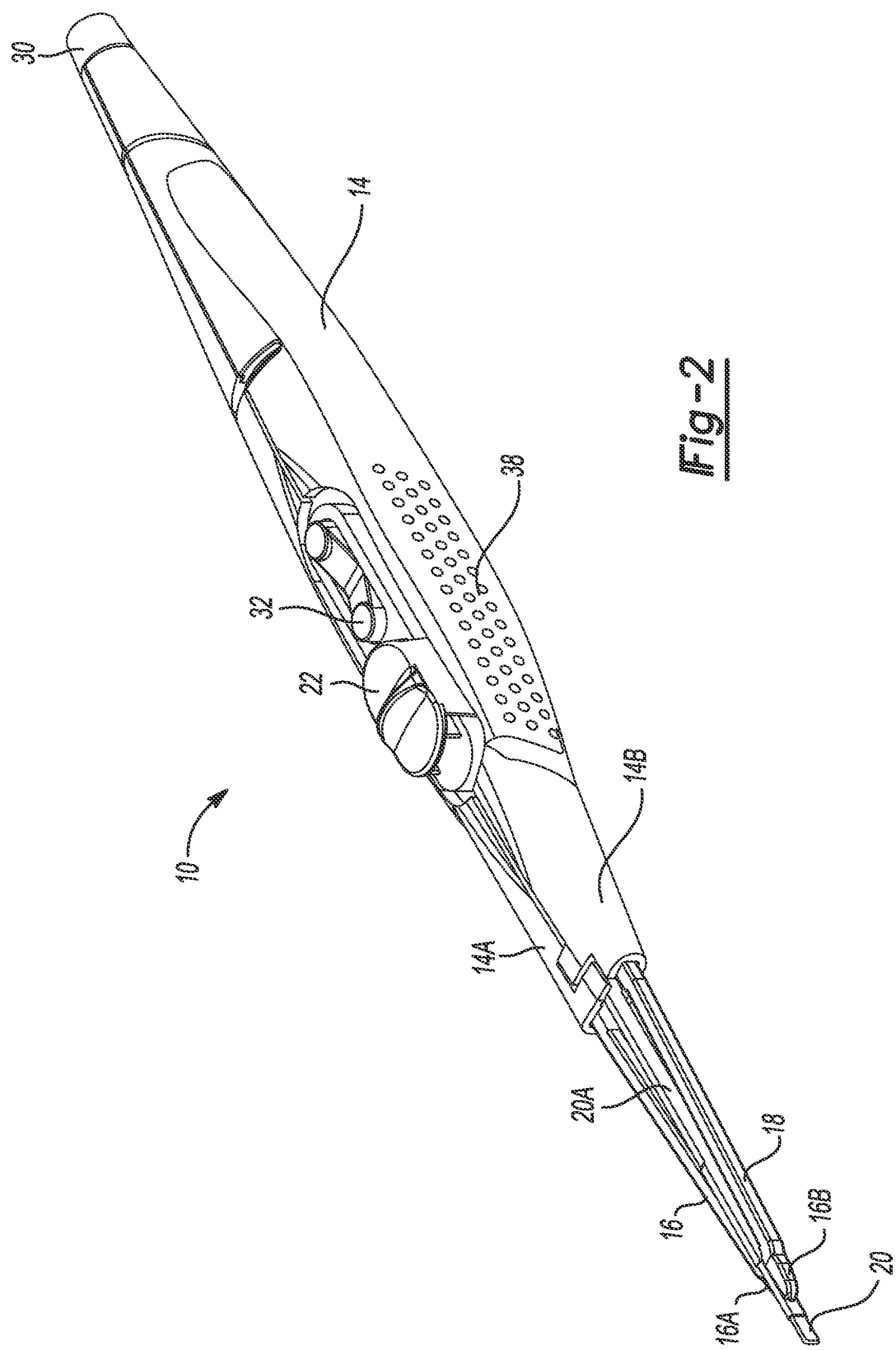
FIG. 2 is a front perspective view of the combination medical device in a second mode of operation according to the principles of the present invention.
Figure 3:
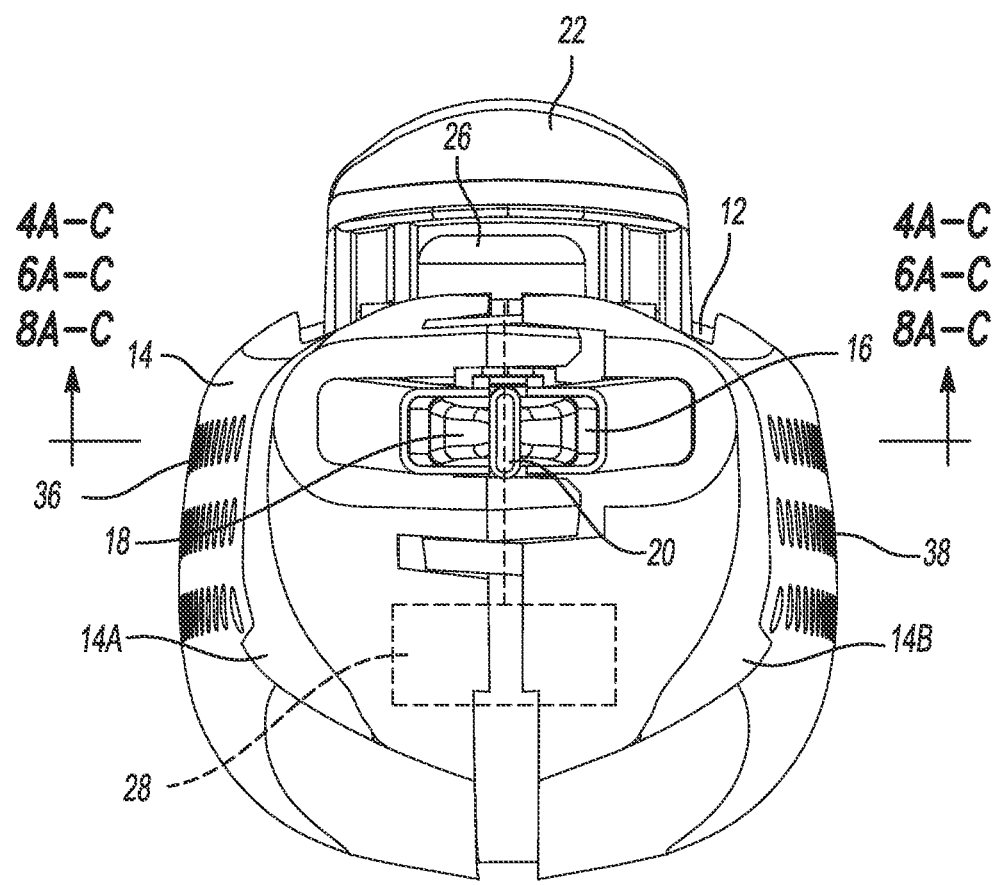
FIG. 3 is a front view of the combination medical device.

With reference to FIGS. 1-3, a combination medical device or forceps according to the principles of the present invention is illustrated and generally indicated by reference number 10. The combination medical device 10 is a surgical tool that may be used in open surgery on a patient. The combination medical device 10 may be used as an electro-surgical tool or as a gripping tool, or both. As an electro-surgical tool, the combination medical device 10 provides a mono-polar or bi-polar therapy current through a tissue and may be used to cut, perform hemostasis on, coagulate, desiccate, fulgurate, electro cauterize, or combinations thereof, tissue of a patient. As a gripping tool the combination medical device 10 is used as forceps or tweezers to grip or retract an object, a vein, an organ, skin, tissue and the like, or combinations thereof. As will be described in greater detail below, the combination medical device 10 also has a first configuration that provides a consistent, constant closure force to grip and a second configuration that provides a consistent, constant opening force that opposes the closure force. The opening force may be overcome by a user of the combination medical device 10 to manually close the combination medical device 10.

The combination medical device 10 generally includes an inner housing 12, an outer housing 14, a first working arm 16, a second working arm 18, and a blade 20. In one example, the blade 20 is a blade electrode used for applying a therapy current to tissue. In another example, the blade 20 is a scalpel used to cut tissue. In alternate embodiments, the blade 20 may be omitted from the combination medical device 10. The inner housing 12 supports a switch 22 that is axially moveable between a first position, shown in FIG. 1, and a second position, shown in FIG. 2. The switch 22 is operatively interconnected with the blade electrode 20 through a biasing mechanism or member 24, shown in various embodiments in FIGS. 4A-9C, as will be described in greater detail below. When the switch 22 is in the first position, the blade 20 does not extend axially past distal ends 16A, 18A of the working arms 16 and 18, respectively. When the switch 22 is in the second position, the blade 20 extends axially past the distal ends 16A, 18A of the working arms 16, 18 and is gripped by the working arms 16, 18.

A first or bi-polar button 26 is mounted to the inner housing 12 and is exposed when the switch 22 is in the first position. The bi-polar button 26 is covered by the switch 22 when the switch 22 is in the second position. The bi-polar button 26 is connected to control hardware 28, shown schematically in FIG. 3. The control hardware 28 is connected to or in electrical communication with a power connector 30 and to the first working arm 16, the second working arm 18, and the blade electrode 20. The power connector 30 is mounted to the inner housing 12 and is connectable to an electrical power source (not shown). The control hardware 28 generally includes circuit boards, control logic, sensors, wires or other power connection mechanisms sufficient to selectively transmit a therapy current from the power source, via the power connector 30, to the first arm 16, the second arm 18, the blade electrode 20, and various combinations thereof. For example, when the bi-polar button 26 is depressed by a user of the combination medical device 10, a first therapy current is transmitted from the power connector 30 to the first working arm 16 and the second working arm 18. Thus, any object disposed between the first working arm 16 and the second working 18 is subjected to this therapy current.

A second or mono-polar button 32 is mounted to the inner housing 12 and is exposed when the switch 22 is in the second position. The mono-polar button 32 is covered by the switch 22 when the switch 22 is in the second position. The mono-polar button 32 is connected to the control hardware 28. When the mono-polar button 32 is depressed by a user of the combination medical device 10, a second therapy current is transmitted from the power connector 28 to the blade electrode 20. Thus, any object disposed proximate to or in contact with the blade electrode 20 is subjected to this therapy current. An example of the connections between the switch 22, the buttons 26 and 32, the control hardware 28, and the working arms 16, 18 and blade electrode 20 are disclosed in commonly assigned U.S. patent application Ser. No. 14/205,598 filed on Mar. 12, 2014, herein incorporated by reference in its entirety.

The outer housing 14 at least partially surrounds the inner housing 12 and is at least partially bifurcated into two halves including a first half 14A and a second half 14B. The first half 14A is hinged or pivotally connected to the second half 14B. The first half 14A supports and at least partially surrounds the first arm 16. The first half 14A of the housing 14 provides a grasping surface 36 for a user of the combination medical device 10 and insulates a user from any therapy current supplied to the first arm 16. The second half 14B supports and at least partially surrounds the second arm 18. The second half 14B of the housing 14 provides a grasping surface 38 for a user of the combination medical device 10 and insulates a user from any therapy current supplied to the second arm 18. The first half 14A and the second half 14B, as well as the working arms 16, 18, are moveable between an open position, shown in FIG. 1, and a closed position, shown in FIG. 2.

With reference to FIGS. 4A-C, the first working arm 16 is an elongated member having a proximate end 16B opposite the distal end 16A. The distal end 16A includes a gripping surface 40 that may be smooth, ridged, lined, ribbed, toothed, serrated, etc. The second working arm 18 is an elongated member having a proximate end 18B opposite the distal end 18A. The distal end 18A includes a gripping surface 42 that may be smooth, ridged, lined, ribbed, toothed, serrated, etc. The gripping surface 42 of the second working arm 18 is disposed opposite the gripping surface 40 of the first working arm 16. The proximate end 16B of the first working arm 16 is interconnected to the proximate end 18B of the second working arm 18. The first working arm 16 and the second working arm 18 are biased towards one another by a closing force Fc. The closing force Fc is sufficient to grip and hold tissue. The working arms 16, 18 may be either resilient or rigid. Generally speaking, a resilient member is flexible and deforms upon application of a force or load. The resilient member then returns to its original shape when the force or load is removed. In contrast, a force or load sufficient to bend a resilient member will not bend, deform, or flex a rigid member. In a preferred embodiment, a rigid member does not deflect or deform under normal operating loads. The working arms 16, 18 may be made of any material that is safe for use in a surgical procedure. For example, the working arms 16, 18 may include metals, plastics, a polymer, an elastomer, gold, silver, copper, titanium, aluminum, iron based metals, stainless steel, and have coatings of polytetrafluoroethylene, insulating polymers, rubber, silicone or a combination thereof.

The blade electrode 20 is interconnected to the switch 22 through the biasing mechanism 24. The blade electrode 20 is an elongated member having, in one embodiment, a distal end 20A and a base 20B. The distal end 20A may be used to apply a current to tissue during surgery. Alternatively, the distal end 20A may be a scalpel or have a cutting edge that may be used to cut tissue during surgery. The base 20B is connected to the biasing mechanism 24.

The biasing mechanism 24 is disposed between the first working arm 16 and the second working arm 18. The biasing mechanism 24 includes a first connector 50, a second connector 52, and a shuttle 54. The first connector 50 and the second connector 52 may be either resilient or rigid. At least one of the first connector 50, the second connector 52, the first working arm 16, and the second working arm 18 is resilient. For example, in one embodiment, both the first connector 50 and the second connector 52 are resilient while the first working arm 50 and the second working arm 52 are rigid. In yet another embodiment, both the first connector 50 and the second connector 52 are rigid while the first working arm 50 and the second working arm 52 are resilient. In yet another embodiment, the first connector 50, the second connector 52, the first working arm 16, and the second working arm 18 are all resilient.

The first connector 50 includes a first end 50A and a second end 50B disposed opposite the first end 50A. The first connector 50 may be straight between the first and second ends 50A, 50B, or the first connector 50 may be curved between the first and second ends 50A, 50B having a concave side 50C proximate the distal end 16A of the first arm 16 and a convex side 50D adjacent the proximate end 16B of the first arm 16. The first end 50A is pivotally connected to the first arm 16 at a pivot point 56. In the example provided, the pivot point 56 is a pin connection that allows the first connector 50 to rotate with respect to the first arm 16. The second end 50B includes a first stop surface 50E and a pivot point 58.

The second connector 52 includes a first end 52A and a second end 52B disposed opposite the first end 52A. The second connector 52 may be straight between the first and second ends 52A, 52B or the second connector 52 may be curved between the first and second ends 52A, 52B having a concave side 52C proximate the distal end 18A of the second arm 18 and a convex side 52D adjacent the proximate end 18B of the second arm 18. The first end 52A is pivotally connected to the second arm 18 at a pivot point 60. In the example provided, the pivot point 60 is a pin connection that allows the second connector 52 to rotate with respect to the second arm 18. The second end 52B includes a second stop surface 52E. The second end 52B of the second connector 52 is pivotally connected to the second end 50B of the first connector 50 at the pivot point 58. Both the first connector 50 and the second connector 52 are pivotally connected to the shuttle 54 at the pivot point 58. The shuttle 54 is interconnected to the switch 22 (FIGS. 1-3).

The biasing mechanism 24 is moveable by the switch 22 to a first position, shown in FIGS. 4A and 4B, and a second position, shown in FIG. 4C. In the first position, the shuttle 54 is moved (to the left in FIG. 4A) towards the proximate ends 16B, 18B. In this position, the stop surfaces 50E and 52E contact each other and the first and second connectors 50, 52 bias the first working arm 16 and the second working arm 18 away from each other to the open position with an opening force $F_o$. The opening force $F_o$ is greater than the closing force Fc of the first and second working arms 16, 18.

In the first position, the combination medical device 10 may act as tweezers or forceps and be manually closed by applying a manual force Fm to the first and second working arms 16, 18 to grab tissue 62 or any other object, as illustrated in FIG. 4B. The closing force Fc and the manual force Fm overcome the opening force Fo to close the first and second working arms 16, 18 by either flexing the first and second connectors 50, 52, flexing the first and second working arms 16, 18, or any combination thereof. The stop surfaces 50E, 52E prevent the shuttle 54 from moving further to the left under compressive forces. The location of the pivot point 58 in turn limits the free movement of the shuttle 54 to the right. For example, the pivot point 58 is located further proximal than an imaginary line connecting the pivot points 56 and 60. As the pivot point 58 moves past the imaginary line connecting the pivot points 56 and 60, the arms 16 and 18 are spread further apart which is opposed by the closing force Fc and therefore the shuttle 54 is prevented from moving freely to the right.

In the second position, the shuttle 54 is moved (to the right in FIG. 4C) towards the distal ends 16A, 18A by the switch 22. In this position, the stop surfaces 50E and 52E do not contact each other and the first and second connectors 50, 52 do not exert a force on the first working arm 16 and the second working arm 18 opposite the closing force Fc. Therefore, the blade electrode 20 is extended out past the working arms 16, 18 and the working arms 16, 18 close on the blade electrode 20, as shown in FIG. 4C.

With reference to FIGS. 5A-C, the combination medical device 10 is schematically illustrated with the blade electrode 20 omitted. In this configuration, the biasing member 24 may be flipped to reverse the first and second positions. For example, the biasing mechanism 24 is moveable by the switch 22 to a first position, shown in FIGS. 5A and 5B, and a second position, shown in FIG. 5C. In the first position, the shuttle 54 is moved (to the right in FIG. 5A) towards the distal ends 16A, 18A. In the first position, the combination medical device 10 may act as tweezers or forceps and be manually closed by applying a manual force $F_m$ to the first and second working arms 16, 18 to grab tissue 62 or any other object, as illustrated in FIG. 4B. The closing force $F_c$ and the manual force $F_m$ overcome the opening force $F_o$ to close the first and second working arms 16, 18 by either flexing the first and second connectors 50, 52, flexing the first and second working arms 16, 18, or any combination thereof. In the second position, the shuttle 54 is moved (to the left in FIG. 5C) towards the proximate ends 16B, 18B by the switch 22. In this position, the stop surfaces 50E and 52E do not contact each other and the first and second connectors 50, 52 do not exert a force on the first working arm 16 and the second working arm 18 opposite the closing force Fc. Therefore, the working arms 16, 18 close on the tissue 62 with the constant, consistent closing force $F_c$, as shown in FIG. 5C.

Turning now to FIGS. 6A-C, an alternate embodiment of a biasing mechanism is generally indicated by reference number 124. The biasing mechanism 124 is disposed between the first working arm 16 and the second working arm 18. The biasing mechanism 124 includes a first connector 150, a second connector 152, and a shuttle 154. The first connector 150 includes a first end 150A and a second end 150B disposed opposite the first end 150A. The first connector 150 is curved between the first and second ends 150A, 150B having a concave side 150C proximate the distal end 16A of the first arm 16 and a convex side 150D adjacent the proximate end 16B of the first arm 16. The first end 150A is pivotally connected to the first arm 16 at a pivot point 156. In the example provided, the pivot point 156 is a pin connection that allows the first connector 150 to rotate with respect to the first arm 16. The second end 150B includes a first stop surface 150E and is pivotally connected to the shuttle 154 at a pivot point 158. In the example provided, the pivot point 158 is a pin connection that allows the first connector 150 to rotate with respect to the shuttle 154.

The second connector 152 includes a first end 152A and a second end 152B disposed opposite the first end 152A. The second connector 152 is curved between the first and second ends 152A, 152B having a concave side 152C proximate the distal end 18A of the second arm 18 and a convex side 152D adjacent the proximate end 18B of the second arm 18. The first end 152A is pivotally connected to the second arm 18 at a pivot point 160. In the example provided, the pivot point 160 is a pin connection that allows the second connector 152 to rotate with respect to the second arm 18. The second end 152B includes a second stop surface 152E. The second end 152B of the second connector 152 is pivotally connected to the shuttle 154 at the pivot point 161. In the example provided, the pivot point 161 is a pin connection that allows the second connector 152 to rotate with respect to the shuttle 154. The shuttle 154 is interconnected to the switch 22 (FIGS. 1-3). The pivot points 158, 161 are proximal to an imaginary line that connects pivot points 156 and 160. The biasing mechanism 124 operates in a manner substantially similar to the biasing mechanism 24 and is moveable between a first position, illustrated in FIGS. 5A and 5B, and a second position, illustrated in FIG. 5C.

With reference to FIGS. 7A-C, the combination medical device 10 having the biasing member 124 is schematically illustrated with the blade electrode 20 omitted. The biasing mechanism 124 is moveable by the switch 22 to the first position, shown in FIGS. 7A and 7B, and the second position, shown in FIG. 7C. In the first position, the shuttle 154 is moved (to the left in FIG. 7A) towards the proximate ends 16B, 18B. In the first position, the combination medical device 10 may act as tweezers or forceps and be manually closed by applying a manual force Fm to the first and second working arms 16, 18 to grab tissue 62 or any other object, as illustrated in FIG. 7B. The closing force Fc and the manual force Fm overcome the opening force Fo to close the first and second working arms 16, 18 by either flexing the first and second connectors 150, 152, flexing the first and second working arms 16, 18, or any combination thereof. In the second position, the shuttle 154 is moved (to the right in FIG. 7C) towards the distal ends 16A, 18A by the switch 22. In this position, the stop surfaces 150E and 152E do not contact each other and the first and second connectors 150, 152 do not exert a force on the first working arm 16 and the second working arm 18 opposite the closing force Fc. Therefore, the working arms 16, 18 close on the tissue 62 with the constant, consistent closing force Fc, as shown in FIG. 7C. The combination medical device 10 may thus act as normal tweezers where the gripping force is determined by the user, or as a mechanical latch where the gripping force is determined by the properties of the device 10.

Turning now to FIGS. 8A-C, an alternate embodiment of a biasing mechanism is generally indicated by reference number 224. The biasing mechanism 224 is disposed between the first working arm 16 and the second working arm 18. The biasing mechanism 224 includes a first connector 250, a second connector 252, and a shuttle 254. The first connector 250 includes a first end 250A and a second end 250B disposed opposite the first end 250A. The first connector 250 is curved between the first and second ends 250A, 250B having a concave side 250C proximate the distal end 16A of the first arm 16 and a convex side 250D adjacent the proximate end 16B of the first arm 16. The first end 250A is pivotally connected to the first arm 16 at a pivot point 256. In the example provided, the pivot point 256 is a hinge that allows the first connector 250 to pivot with respect to the first arm 16. The pivot point 256 has a narrow cross section which bows or flexes during the pivot. The pivot point 256 may be made integrally with the first working arm 16 or be welded, adhered, or otherwise connected to the first working arm 16. The second end 250B includes a first stop surface 250E and is pivotally connected to the shuttle 254 and the second connector 252 at a pivot point 258. The pivot point 258 has a narrow cross section which bows or flexes during the pivot. The pivot point 258 is preferably integrally formed with the second connector 252 and may be made integrally with the shuttle 254 or be welded, adhered, or otherwise connected to the shuttle 254.

The second connector 252 includes a first end 252A and a second end 252B disposed opposite the first end 252A. The second connector 252 is curved between the first and second ends 252A, 252B having a concave side 252C proximate the distal end 18A of the second arm 18 and a convex side 252D adjacent the proximate end 18B of the second arm 18. The first end 252A is pivotally connected to the second arm 18 at a pivot point 260. In the example provided, the pivot point 260 is a hinge that allows the second connector 252 to pivot with respect to the second arm 18. The pivot point 260 has a narrow cross section which bows or flexes during the pivot. The pivot point 260 may be made integrally with the second working arm 18 or be welded, adhered, or otherwise connected to the second working arm 18. The second end 252B includes a second stop surface 252E. The second end 252B of the second connector 252 is pivotally connected to the shuttle 254 at the pivot point 258. The shuttle 154 is interconnected to the switch 22 (FIGS. 1-3). The biasing mechanism 224 operates in a manner substantially similar to the biasing mechanism 24 and is moveable between a first position, illustrated in FIGS. 8A and 8B, and a second position, illustrated in FIG. 8C.

With reference to FIGS. 9A-C, the combination medical device 10 having the biasing member 224 is schematically illustrated with the blade electrode 20 omitted. The biasing mechanism 224 is moveable by the switch 22 to the first position, shown in FIGS. 9A and 9B, and the second position, shown in FIG. 9C. In the first position, the shuttle 254 is moved (to the left in FIG. 9A) towards the proximate ends 16B, 18B. In the first position, the combination medical device 10 may act as tweezers or forceps and be manually closed by applying a manual force $F_m$ to the first and second working arms 16, 18 to grab tissue 62 or any other object, as illustrated in FIG. 9B. The closing force $F_c$ and the manual force $F_m$ overcome the opening force $F_o$ to close the first and second working arms 16, 18 by either flexing the first and second connectors 250, 252, flexing the first and second working arms 16, 18, or any combination thereof. In the second position, the shuttle 254 is moved (to the right in FIG. 9C) towards the distal ends 16A, 18A by the switch 22. In this position, the stop surfaces 250E and 252E do not contact each other and the first and second connectors 250, 252 do not exert a force on the first working arm 16 and the second working arm 18 opposite the closing force $F_c$. Therefore, the working arms 16, 18 close on the tissue 62 with the constant, consistent closing force $F_c$, as shown in FIG. 9C.

Turning to FIGS. 10A-C, an alternate arrangement of the combination medical device 10 is schematically illustrated with the blade electrode 20 omitted and the biasing member 24 rotated to actuate outside of the plane of the first and second working arms 16, 18. For example, the shuttle 54 may be interconnected to a switch or button (not shown) located on a side of the outer housing 14 such that the shuttle 54 is actuated not on a plane defined by the first working arm 16 and the second working arm 18. For example, the shuttle 54 is actuated perpendicular to the plane defined by the first working arm 16 and the second working arm 18. For example, the shuttle 54 is actuated perpendicular to the plane defined by the first working arm 16 and the second working arm 18. The biasing mechanism 24 is moveable by the button to a first position, shown in FIGS. 10A and 10B, and a second position, shown in FIG. 10C. In the first position, the biasing member 24 is in the plane defined by the first and second working arms 16 18, as shown in FIG. 11A. In the first position, the combination medical device 10 may act as tweezers or forceps and be manually closed by applying a manual force Fm to the first and second working arms 16, 18 to grab tissue 62 or any other object, as illustrated in FIG. 10B. The closing force Fc and the manual force Fm overcome the opening force Fo to close the first and second working arms 16, 18 by either flexing the first and second connectors 50, 52, flexing the first and second working arms 16, 18, or any combination thereof. In the second position, the biasing member 24 is moved out of the plane defined by the first and second working arms 16, 18 as shown in FIG. 11B. In this position, the stop surfaces 50E and 52E do not contact each other and the first and second connectors 50, 52 do not exert a force on the first working arm 16 and the second working arm 18 opposite the closing force Fc. Therefore, the working arms 16, 18 close on the tissue 62 with the constant, consistent closing force Fc, as shown in FIG. 10C. It should be appreciated that the biasing mechanisms 124, 224 may also be configured in a manner similar to that shown in FIGS. 10A-100 without departing from the scope of the present invention.

The description of the invention is merely exemplary in nature and variations that do not depart from the gist of the invention are intended to be within the scope of the invention. Such variations are not to be regarded as a departure from the spirit and scope of the invention.

The invention claimed is:

1. A device comprising:
   a first arm;
   a second arm interconnected to the first arm, wherein the first arm and the second arm are biased towards each other by a closing force;
   a biasing member disposed between the first arm and the second arm, wherein the biasing member has a first position that biases the first arm and the second arm away from each other against the closing force and a second position that does not oppose the closing force, wherein the biasing member includes a first connector pivotally connected to the first arm and a second connector pivotally connected to the second arm, and wherein the first connector is pivotally connected to the second connector,
   the first connector has a first surface, the second connector has a second surface, and the first surface contacts the second surface when the biasing member is in the first position,
   wherein the first arm has a first distal end and a first proximate end, the second arm has a second distal end and a second proximate end, and the first proximate end is interconnected to the second proximate end to bias the first distal end and the second distal end towards one another, wherein the first connector is connected to the second connector at a pivot point, wherein the pivot point remains on a plane defined by the first arm and the second arm when the biasing member is in the first position and the second position and the pivot point is closer to the first and second distal ends when in the first position than when in the second position.

2. The device of claim 1 further comprising a blade connected at the pivot point, wherein the blade is extended past the first and second distal ends when the biasing member is in the second position and wherein the blade does is not extended past the first and second distal ends when the biasing member is in the first position.

3. The device of claim 1 wherein the pivot point is not on a plane defined by the first arm and the second arm when the biasing member is in at least one of the first position and the second position.

4. A surgical tool comprising:

a first arm;

a second arm interconnected to the first arm, wherein the first arm and the second arm have an open position and a closed position;

a first connector having a first proximate end connected to the first arm and having a first distal end and a first stop surface at the first distal end, wherein the first connector has a concave surface and a convex surface extended between the first distal end and the first proximate end; and a second connector having a second proximate end connected to the second arm, having a second distal end connected to the first distal end of the first connector, and having a second stop surface at the second distal end, wherein the second connector has a concave surface and a convex surface extended between the second distal end and the second proximate end, and wherein the first stop surface contacts the second stop surface and the first and second arms are in the open position when the first member and the second member are in a first position, and wherein the first stop surface does not contact the second stop surface and the first and second arms in the closed position when the first member and the second member are in a second position.

* * * * *